United States Patent [19]

Kataoka et al.

[11] Patent Number: 5,476,998
[45] Date of Patent: Dec. 19, 1995

[54] CULTIVATED MELON WITH A SOUR TASTE AND A PROCESS FOR THE PRODUCTION THEREOF

[75] Inventors: Setsuo Kataoka, Tokyo; Yurie Shintaku, Musashi Plant Breeding Corp., 3-4-19, Kami-shakujii, Nerima-ku, Tokyo, both of Japan

[73] Assignee: Yurie Shintaku, Tokyo, Japan

[21] Appl. No.: 131,304

[22] Filed: Oct. 4, 1993

[30] Foreign Application Priority Data

Oct. 6, 1992 [JP] Japan ................. 4-267709

[51] Int. Cl.⁶ .................. A01G 1/00; A01H 1/02; A01H 5/00; A01H 5/08
[52] U.S. Cl. .................. 800/200; 800/255; 800/DIG. 19; 47/58; 47/DIG. 1
[58] Field of Search .................. 800/200, 205, 800/250, 255, DIG. 19; 47/58, DIG. 1

[56] References Cited

PUBLICATIONS

Aly M. Ibrahim, et al., "'Najd I' and 'Nadj II', Two Sour–sweet Melon Cultivars," HortScience, vol. 27(3), Mar. 1992, pp. 276–277.
Claude E. Thomas, "Downy and Powdery Mildew Resistant Muskmelon Breeding Line MR–1," HortScience, vol. 21(2), Apr. 1986, p. 329.
Claude E. Thomas, "Resistance Reaction of Muskmelon Line MR–1 Against Downey Mildew," Phytophathology 75:504 (1985). p. 504.
Claude E. Thomas, "Resistance to Downy Mildew in *Cucumis melo* Plant Introductions and American Cultivars," Plant Disease/vol. 66, No. 6 (1982), pp. 500–502.
B. Kubicki, "Inheritance of Some Characters in Muscmelons (*Cucumis Melo L.*)," Genetica Polonica, vol. 3(3), (1962), pp. 265–274.
Hussain et al. 1986. Pakistan J. Agric. Res. 7(3):193–197.
Kalb et al. 1984. J. Amer. Soc. Hort. Sci. 109(3):411–415.
Ibrahim et al. 1992. Hort Science. 27(3):276–277.
Webster's II New Riverside University Dictionary. 1988. Soukharov et al., eds. p. 740.

*Primary Examiner*—David T. Fox
*Assistant Examiner*—Erich E. Veitenheimer
*Attorney, Agent, or Firm*—Limbach & Limbach; W. Patrick Bengtsson

[57] ABSTRACT

The present invention relates to an $F_1$ hybrid melon characterized by having a sour taste, produced by crossing a melon having at least one dominant allele for expression of weak-acid pH value in flesh and at least one recessive allele for expression of mealy character in flesh and a cultivated melon having at least one recessive allele for expression of neutral pH value in flesh and at least one dominant allele for expression of juicy character in flesh as well as to a process for the production thereof. According to the present invention, there is provided a novel melon with both sour and sweet tastes.

7 Claims, No Drawings

CULTIVATED MELON WITH A SOUR TASTE AND A PROCESS FOR THE PRODUCTION THEREOF

The present invention relates to a melon characterized by having a sour taste not possessed by present-day cultivated melons, as well as to a process for the production thereof.

BACKGROUND OF THE INVENTION

Melons (scientific name: Cucumis melo L.) produced by the gourd family came originally from the areas along the Niger river in Africa and then distributed from the place of origin to Central Asia (the secondary place for primeval melons) where the varieties of melon were differentiated. Melons spread therefrom to the West to become the "western melon" (referred to as "melon," hereinafter) and the one distributed to the East became the "oriental melon."

Melon is also popular in Japan and a number of different types of melons have been cultivated. However, these cultivated melons have only a sweet taste in a part of the flesh, and no cultivated melons tasting characteristically of a sour taste were known.

SUMMARY OF THE INVENTION

The object of the present invention is to provide a melon of higher value as a commercial product by introducing a sour taste to conventional cultivated melons which generally only have a sweet taste.

As a result of extensive research into the relationship between the pH value and sour taste of melon, the present inventors found that the flesh of melon should have not only a low pH but also a high water content in order to cause the melon fruit to have a sour taste when eaten.

That is, the present invention relates to an $F_1$ hybrid melon characterized by having a sour taste, produced by crossing a melon having at least one dominant allele for expression of weakly-acidic pH value in flesh and at least one recessive allele for expression of mealy character in flesh and a cultivated melon having at least one recessive allele for expression of neutral pH value in flesh and at least one dominant allele for expression of juicy character in flesh.

The present invention further relates to a melon progeny from the above-mentioned $F_1$ hybrid melon, said progeny having at least one dominant allele for expression of weakly-acidic pH value in flesh and at least one dominant allele for expression of juicy character in flesh.

Furthermore, the present invention relates to a process for the production of the above-mentioned $F_1$ hybrid melon.

Said melon progeny includes both hybridized progeny and self-fertilized progeny.

A method of breeding the melon of the present invention and the characteristics thereof are illustrated below.

DETAILED DESCRIPTION OF THE INVENTION (A) Breeding Method

Melon with at least one dominant allele for expression of weakly-acidic pH value in flesh and a recessive allele for expression of mealy character in flesh includes e.g. melon breeding line MR1, line PI124111, etc.

The line PI124111 was gifted from U.S. Vegetable Laboratory, ARS/USDA (2875 Savannah Hwy, Charleston, S.C. 29407, U.S.A.).

The melon breeding line MR1 (referred to "MR1", hereinafter), which is disease-resistant like the line PI124111, was gifted from U.S. Vegetable Laboratory, ARS/USDA (2875 Savannah Hwy, Charleston, S.C. 29407, U.S.A). As shown in Table 1, the flesh of MR1 is mealy (i.e. low water content) and very thin. The MR1, although being tasteless in flesh, has a strong sour taste in seeds-surrounding gelatin-like substance (referred to as "gelatin-like substance," hereinafter) and in placenta.

TABLE 1

| Characteristics of fruit | |
|---|---|
| MR1 | |
| Relative days to maturity | early |
| Weight of fruit | light |
| Surface of fruit | no net |
| Flesh color | white |
| Flesh texture | mealy |
| Thickness of fruit | thin |
| Taste | |
| Flesh | tasteless |
| Gelatin-like substance | sour taste |
| Placenta | sour taste |

MR1 fruits cultured in Japan tend to crack, so that an individual used in hybridization is preferably one bearing few cracking fruits and having a strong sour taste in gelatin-like substance and placenta, selected from progeny having been self-fertilized for several generations.

MR1 is now possessed by the applicant and can be distributed as necessary. A deposit of 2500 seeds for the melon of the present invention was made at the American Type Culture Collection on Jul. 20, 1995. The accession number for the deposit is ATCC No. 97226.

The "cultivated melon" mentioned in the present specification refers to a melon artificially cultivated as a commercial product with only sweetness being free of any sour taste. The cultivated melon used in the present invention is not particularly limited as far as it has at least one recessive allele for expression of neutral pH value and at least one dominant allele for expression of juicy character in flesh. Preferred examples are the purebred line Earl's Favourite or purebred lines resembling Earl's Favourite in appearance and color of flesh and being more easy to produce with a stable sugar content, e.g. the purebred lines Earl's Sine, Andes, Loran (for production of flesh in shades of green), Aurora (for production of flesh in shades of orange), and purebred lines such as Sherry and Homerun (for production of flesh in shades of white) etc.

In the present invention, hybridization may be effected according to a conventional method, without requiring any particular procedure.

The cultivation of the melon produced according to the present invention may be effected in a usual manner, without requiring any particular procedure.

(B) Characters

The $F_1$ hybrid melons produced according to the present invention possess the following characteristics.

The characters of $F_1$ melons obtained from a cross between MR1 and a wide variety of cultivated melons are set forth in Table 2. Common characteristics among the $F_1$ melons are as follows:

The $F_1$ melons have no or very rough net regardless of the presence of a net on the surface of the cultivated melon as a parent fruit and the density of the net. Most of the $F_1$, like MR1, have a pale green pericarp, but the $F_1$ progeny of a cross with dark green type melon have a slightly dark green flesh in some cases. The fruits of $F_1$ are globular or spindle-shaped. The $F_1$ progeny of a cross with MR1 have slight ribs on the fruit exterior have no or slight ribs on the exterior. The thickness of $F_1$ flesh lies between those of their parents. The color of $F_1$ flesh varies depending on the color of their parents: cultivated melons with a white-colored flesh yield $F_1$ being white-colored toward the flesh and pale orange-colored toward the seeds; those with a green-colored flesh yield $F_1$ being green-colored toward the flesh and pale orange-colored toward the seeds; and those with an orange or reddish orange flesh yield $F_1$ with an orange- or reddish orange-colored flesh. In each case, the gelatin-like substance is orange-colored.

The $F_1$ plants generally resemble the cultivated melon as their parent in plant vigor, leaf size, and leaf color. Long length between nodes, one of the characters of MR1, occurs in the $F_1$ progeny produced in every combination of crossing. The $F_1$ progeny grow early, so that the period of time from flowering to fruit maturing is short, as is the case with MR1. MR1 is a monoecious line, and the resulting $F_1$ is also monoecious.

TABLE 2

Characteristics of $F_1$ fruits between cultivated melon and MR1-$S_3$

| (Characters) | No. AxMR1-$S_2$ | No. BxMR1-$S_2$ | No. CxMR1-$S_2$ | No. DxMR1-$S_2$ |
| --- | --- | --- | --- | --- |
| Seed size | medium | medium | medium | medium |
| Length between nodes of a main vine | long | long | long | long |
| Leaf size | medium | medium | medium | medium |
| Leaf lobation | shallow | shallow | shallow | shallow |
| Leaf color | green | green | green | green |
| Length of petiole | medium | medium | medium | medium |
| Flower type | monoecious | monoecious | monoecious | monoecious |
| Location for adhension of female flower | the first node of main vine, sedondary vine, and tertiary vine | the first node of main vine, secondary vine, and tertiary vine | the first node of main vine, secondary vine, and tertiary vine | the first node of main vine, secondary vine, and tertiary vine |
| Occurrence of male flower for spring harvest | good | good | good | good |
| Occurrence of male flower for autumn harvest | medium | medium | medium | medium |
| Flesh color (when ripen) | yellowish green | grayish green | green | pale green |
| Fruit shape | spindle-shaped | globular | globular | globular |
| Fruit exterior | slightly ribbed | slightly ribbed | slightly ribbed | slightly ribbed |
| Density of net (when ripen) | rough or absent | rough or absent | rough or absent | rough or absent |
| Period for ripening | early-ripening | early-ripening | early-ripening | early-ripening |
| Mean fruit weight | 1.7 kg | 1.1 kg | 1.4 kg | 1.4 kg |
| Flesh color Flesh near pericarp | white/yellow/green | green | yellow/green | green |
| Flesh in the middle position | green | white/green/pale orange | green/pale orange | pale orange/orange |
| Flesh near seeds | pale orange | white/green/pale orange | yellow/pale orange | pale orange/orange |
| Color of gelatin-like substance around seeds | pale orange | pale orange | pale orange | orange |
| Flesh texture (when ripen) | sticky-mealy | crisp | melting | melting |
| Mean thickness of flesh | 3.4 cm | 2.8 cm | 2.9 cm | 2.8 cm |
| Total soluble solids content (°Brix) | 8.4 | 11.1 | 8.9 | 7.8 |
| Mean pH value | 4.9 | 4.8 | 4.6 | 4.7 |
| Flavor | netted melon | netted melon | netted melon | carotene |
| Keeping quality | medium | medium | medium | medium |
| Disease-resistance to Powdery mildew (whole year) | resistance | resistance | resistance | resistance |
| Powdery mildew (spring) | resistance | resistance | resistance | resistance |
| Fusarium wilt | tolerance | tolerance | tolerance | tolerance |
| Gummy stem | tolerance | tolerance | tolerance | tolerance |

TABLE 2-continued

| (Characters) | Characteristics of $F_1$ fruits between cultivated melon and MR1-$S_3$ | | | |
|---|---|---|---|---|
| | No. AxMR1-$S_2$ | No. BxMR1-$S_2$ | No. CxMR1-$S_2$ | No. DxMR1-$S_2$ |
| bright | | | | |
| Downy mildew | tolerance | tolerance | tolerance | tolerance |
| CMV | medium | medium | medium | medium |
| Physiological wilt | medium | medium | medium | medium |
| Plant vigor | weak | strong | medium | medium |

The present invention is further described in detail with reference to the following Examples.

Test Example 1

A test was carried out in order to examine the sour taste of melon flesh according to the procedure as described below:

1. pH measurement in the flesh of cultivated melon and MR1

In 1991, measurements were made of the pH values in 3 parts of the fruits from the self-fertilized $S_3$ generation of MR1 (MR1-$S_3$) and the cultivated melons Nos. A and B. Whatman pH test papers (pH 3.8–5.5, pH 5.2–6.8, and pH 6.0–8.1) were used for the pH measurement, and juices from (1) seeds and gelatin-like substance around seeds, (2) placenta, and (3) flesh, were examined.

TABLE 3

| | Taste and pH values in 3 parts of fruits | | |
|---|---|---|---|
| No. of line | cultivated melon | | melon for crossing |
| | A | B | MR1-$S_3$ |
| Number of individuals examined | 6 | 5 | 9 |
| Fruit texture | juicy | juicy | mealy |
| Fruit taste | sweet pH6.6 | sweet pH6.1 | tasteless pH4.9 |
| | (mean pH: 6.4) | | |
| Gelatin-like substance | sweet pH6.4 | sweet pH6.1 | sour pH4.6 |
| | (mean pH: 6.4) | | |
| Placenta | sweet pH6.5 | sweet pH6.3 | sour pH4.8 |
| | (mean pH: 6.4) | | |
| Mean pH | pH6.5 | pH6.2 | pH4.8 |
| | (mean pH: 6.4) | | |

As shown in Table 3, the cultivated melons A and B had only sweetness free of any sour taste in each part of gelatin-like substance, placenta, and flesh, with an approximately neutral pH value of 6.4 (=mean pH in 3 parts). On the other hand, MR1-$S_3$ had a strong sour taste, particularly in the placenta and next to the gelatin-like substance, but its flesh was tasteless without any sour or sweet taste. The pH was decreased in the order of flesh, placenta, and gelatin-like substance (pH 4.9, pH 4.8, and pH 4.6). These results indicate that (1) the flesh of MR 1-$S_3$, although being free of any sour taste, has such a low pH value as 4.9, and (2) the order of decreasing sour taste (i.e., placenta, gelatin-like substance, and flesh) does not agree with the order of decreasing pH value (i.e., flesh, placenta, and gelatin-like substance). The flesh of MR1-$S_3$ is so mealy that no juice flows from a cut site of fruit, and the presence of juice (water content) can hardly be recognized in the flesh when eaten. Its water content was higher in the gelatin-like substance and placenta, particularly in the placenta, as compared with the flesh. That is, the recognized sour taste was increased in the order of increasing water content (i.e., flesh, gelatin-like substance, and placenta).

The sense of taste is elucidated to occur when chemical substances and ions, in a state of being dissolved in water, come in contact with papillae. Hence, the reason for a lack of any sour taste in the flesh of MR1-$S_3$ is assumed to be due to a considerably low content of juice (water content) in the flesh, as compared with gelatin-like substance and the placenta.

2. Determination of the contents of juice and solids in flesh of MR1 and $F_1$ melons It was investigated for confirmation of the above assumption whether or not there is any difference in water content between flesh of MR1 and $F_1$ melons.

Three individuals free of any sour taste in the flesh from the self-fertilized $S_4$ generation of MR1 (MR1-$S_4$) (the mealy texture, with the sour taste degree of 0) were obtained in 1992, and 5 individuals (the juicy-texture, with the sour taste degree of 3) whose flesh has a strong sour taste with such a pH range as in MR1-$S_4$ were selected from progeny from a cross between No. 2 and MR1. From them, a predetermined volume of flesh was cut out with a cork borer, then placed in a mortar, and disrupted with a pestle. Subsequently, the flesh thus sufficiently disrupted was introduced in a centrifuge tube with a cap, followed by centrifugation for 20 minutes at 3,500 rpm. After the centrifugation, the volume of juice and the volume (content) of solids were recorded.

TABLE 4

| | Ratio of volume of juice/volume of solids in flesh | | | | |
|---|---|---|---|---|---|
| Sample No. | pH | Degree of sour taste | Volume (A) of juice | Volume(B) of solids | % (A/B) |
| MR1-$S_4$ (mealy) | | | | | |
| 1 | 4.3 | 0 | 7.0ml | 4.4ml | 159 |
| 2 | 4.7 | 0 | 7.8 | 5.2 | 146 |
| 3 | 4.6 | 0 | 7.4 | 4.1 | 180 |
| $F_1$ melon (juicy) | | | | | |
| 1 | 4.3 | 3 | 6.6 | 2.2 | 300 |
| 2 | 4.6 | 3 | 7.6 | 2.3 | 304 |
| 3 | 4.3 | 3 | 7.5 | 2.5 | 300 |
| 4 | 4.8 | 3 | 8.2 | 2.0 | 410 |
| 5 | 4.6 | 3 | 8.2 | 2.3 | 357 |

Table 4 indicates that in the mealy-type MR1–$S_4$ melon the content of solids exceeds the volume of juice, as opposed to the case with the juicy-type $F_1$ melon. An inadequate juice content (water content) in the flesh is considered to make it impossible for us to recognize the sour taste corresponding to its actual pH. That is, besides the actual pH, the flesh texture (i.e., juicy-type or mealy-type) was considered to affect the recognition of sour taste. Hence, it can be understood that a melon with a sour taste is obtainable from the progeny having the juicy-type flesh of low pH from a cross between a cultivated melon having the juicy-type flesh of neutral pH and a MR1 melon having the mealy-type, weakly acid flesh, although neither parent has any sour taste.

Test Example 2

The inheritance of characters from MR1 was examined according to the following procedure:
1. Evaluation of a gene governing the pH of flesh As a result of examinations made of the $F_1$ generation from a cross in 1987 between MR1 and the cultivated melon, it was found that the $F_1$ had a new taste completely different from that of conventional melons; i.e. its flesh had both sour and sweet tastes in spite of a lack of any sour taste in the flesh of its parents.

Since the presence of a sour taste was found in the flesh from the $F_1$ generation, we decided to examine its pH value. For production of the $F_1$ melons, $F_1$ seeds were obtained in 1990 by crossing of the self-fertilized $S_2$ generation of MR1 (MR1–$S_2$) and the cultivated melon No. A, B, or C, and were sown in 1992 to yield $F_1$ melons. Measurements were made of the pH value of the flesh from the $F_1$ melons thus obtained.

TABLE 5

| Degree of acidity, pH value, of the fruits in $F_1$ generation | | | | |
|---|---|---|---|---|
| | Number of individuals | Flesh texture | pH value | Degree of sour taste |
| cultivated melon | | | | |
| No. A | 6 | juicy-type | 6.5 | 0 (no sour taste) |
| No. B | 5 | juicy-type | 6.2 | 0 (no sour taste) |
| No. C | 4 | juicy-type | 6.4 | 0 (no sour taste) |
| MR1-$S_2$ | | | | |
| No. 1 | 1 | mealy-type | 4.9 | 0 (no sour taste) |
| No. 2 | 1 | mealy-type | 4.7 | 0 (no sour taste) |
| No. 3 | 1 | mealy-type | 4.7 | 0 (no sour taste) |
| $F_1$ | | | | |
| No. AxMR1-No. 1 | 14 | juicy-type | 4.9 | 1.4 (sour taste) |
| No. BxMR1-No. 2 | 13 | juicy-type | 4.6 | 2.8 (strong sour taste) |
| No. CxMR1-No. 3 | 10 | juicy-type | 4.3 | 3 (strong sour taste) |

1) The strength of sour taste is indicated as the degree of sour taste which is assigned "0" where no sour taste is present and "3" where a strong sour taste is present.

As can be seen from Table 5, the $F_1$ melons exhibited the property of weak acidity in the flesh. This indicates that the property of weak acidity is dominantly inherited.

In 1990, the self-fertilized $S_2$ generation of MR1 (MR1–$S_2$) was hybridized with the cultivated melon No. A or B, whereby $F_1$ seeds were obtained. In the spring of the following year (1991), a part of the seeds were sown, so that $F_2$ seeds were obtained. In the summer of 1991, a part of the $F_2$ seeds were sown, whereby $F_3$ seeds were obtained. In 1992, the $F_2$ and $F_3$ seeds were sown. The resulting melons were measured for the pH value of their flesh.

If it is assumed from analysis of $\chi^2$ for the $F_2$ segregation ratio that the weak acidity of flesh is controlled by one dominant allele, the marginal pH value for recognition of its sour taste must be present in the ranges of pH 5.0–5.2 and pH 4.8–5.2 (Table 6) or pH 5.0–5.1 (Table 7) in order to conform to the $F_2$ segregation ratio. However, since there was no actual sour taste in the flesh of such pH ranges, said assumption was abandoned. Another assumption that the weak acidity of flesh is subject to control by two dominant alleles plus one recessive allele ($F_2$ segregation ratio: 45:19) or by one dominant allele plus two recessive alleles ($F_2$ segregation ratio: 36:28=9:7) was also abandoned for the same reason as described above. The marginal pH value for recognition of its sour taste must be present in the range of pH 5.3–6.5 (Table 6) or pH 5.3–6.3 (Table 7) in the case of control by two dominant alleles and in the range of pH 5.8–6.5 (Table 7) in the case of control by three dominant alleles. From the foregoing and the findings (1) the cultivated melon Nos. B, C, and A have pH 6.2, 6.4, and 6.5 in flesh, respectively, (2) the highest pH of F1 melon was pH 5.4, and (3) a tasting test indicated that the hybridized melon progeny with a pH value of 5.8 or more do not have any sour taste, it was considered that the lowest pH value indicated by a progeny free of an MR1-derived gene governing weak acidity would be present from pH 5.8 to neutral pH, so that the weak acidity of flesh is assumed to be controlled by two dominant alleles, three dominant alleles, or more.

TABLE 6

| Evaluation of $\chi_2$ for $F_2$ segregation ratio with respact to weak acidity | | | | | | | | | |
|---|---|---|---|---|---|---|---|---|---|
| | (No. AxMR1-No. 1)$F_2$ | | | | | (No. BxMR1-No. 2) $F_2$ | | | |
| | Number of individuals | | | | | Number of individuals | | | |
| pH | A | B | 3:1 | 15:1 | | A | B | 3:1 | 15:1 |
| 4.0 | 0 | 0 | | | | 0 | 0 | | |
| 4.1 | 0 | 0 | | | | 0 | 0 | | |
| 4.2 | 0 | 0 | | | | 1 | 1 | | |
| 4.3 | 0 | 0 | | | | 4 | 5 | | |
| 4.4 | 0 | 0 | | | | 1 | 6 | | |
| 4.5 | 0 | 0 | | | | 4 | 10 | | |
| 4.6 | 3 | 3 | | | | 5 | 15 | | |
| 4.7 | 5 | 8 | | | | 11 | 26 | 15.4x | |
| 4.8 | 4 | 12 | | | | 13 | 39 | 1.32 | |
| 4.9 | 6 | 18 | 7.36x | | | 2 | 41 | 0.29 | |
| 5.0 | 4 | 22 | 1.22 | | | 4 | 45 | 0.47 | |
| 5.1 | 2 | 24 | 0.091 | | | 3 | 48 | 2.58 | 8.85x |
| 5.2 | 4 | 28 | 1.71 | 4.46x | | 0 | | | |
| 5.3 | 2 | 30 | 4.45x | 0.45 | | 2 | 50 | 4.92x | 3.54 |
| 5.4 | 1 | 31 | | 0.0020 | | 0 | | | |
| 5.5 | 0 | | | | | 0 | | | |
| 5.6 | 1 | 32 | | 0.58 | | 0 | | | |
| 5.7 | 0 | | | | | 4 | 54 | | 0.095 |
| 5.8 | 0 | | | | | 1 | 55 | | 0.73 |
| 5.9 | 0 | | | | | 0 | | | |
| 6.0 | 0 | | | | | 1 | 56 | | 1.97 |
| 6.1 | 0 | | | | | 0 | | | |
| 6.2 | 0 | | | | | 0 | | | |
| 6.3 | 0 | | | | | 0 | | | |

TABLE 6-continued

Evaluation of $\chi_2$ for $F_2$ segregation ratio with respect to weak acidity

| | (No. AxMR1-No. 1)$F_2$ | | | | (No. BxMR1-No. 2) $F_2$ | | | |
|---|---|---|---|---|---|---|---|---|
| | Number of individuals | | | | Number of individuals | | | |
| pH | A | B | 3:1 | 15:1 | A | B | 3:1 | 15:1 |
| 6.4 | 1 | 33 | | 2.20 | 1 | 57 | | 3.80 |
| 6.5 | 0 | | | | 0 | | | |
| | 33 | | | | 57 | | | |

1) On the basis of the analisis of $\chi_2$, the individuals examined were divided into two groups in number in accordance with each $F_2$ segregation ratio. Whether or not said two groups are actually in accordance with the $F_2$ segregation ratio, they were examined for the presence of an acid taste.
2) $F_2$ segregation ratio:
Control by one dominant allele = 3:1.
Control by two dominant alleles = 15:1.
3) $\chi^2{}_{0.05} = 3.84$.
4) A: the number of individuals at each pH value. B: the cumulative total of individuals in the range of pH 4.0–6.5.

TABLE 7

Evaluation of $\chi_2$ for $F_2$ segregation ratio with respect to weak acidity

| | Number of individuals | | | | | | |
|---|---|---|---|---|---|---|---|
| pH | A | B | 3:1 | 15:1 | 63:1 | 45:19 | 36:28 = 9:7 |
| 4.0 | 0 | 0 | | | | | |
| 4.2 | 0 | 0 | | | | | |
| 4.4 | 4 | 5 | | | | | |
| 4.4 | 1 | 6 | | | | | |
| 4.5 | 4 | 10 | | | | | |
| 4.6 | 8 | 18 | | | | | |
| 4.7 | 16 | 34 | | | | | 12.5x |
| 4.8 | 17 | 51 | | | 8.03x | 0.00635 | |
| 4.9 | 8 | 59 | 4.28x | | 0.975 | 3.17 | |
| 5.0 | 8 | 67 | 0.015 | | 0.737 | 12.1x | |
| 5.1 | 5 | 72 | 1.20 | | | 4.05x | |
| 5.2 | 4 | 76 | 4.28x | 13.3x | | | |
| 5.3 | 4 | 80 | | 3.63 | | | |
| 5.4 | 1 | 81 | | 2.16 | | | |
| 5.5 | 0 | | | | | | |
| 5.6 | 1 | 82 | | 1.07 | | | |
| 5.7 | 4 | 86 | | 0.50 | 4.86x | | |
| 5.8 | 1 | 87 | | 1.31 | 1.83 | | |
| 5.9 | 0 | | | | | | |
| 6.0 | 1 | 88 | | 2.49 | 0.25 | | |
| 6.1 | 0 | | | | | | |
| 6.2 | 0 | | | | | | |
| 6.3 | 0 | | | | | | |
| 6.4 | 2 | 90 | | 6x | 1.43 | | |
| 6.5 | 0 | | | | | | |
| | 33 | | | | | | |

1) On the basis of the analysis of $\chi_2$, the individuals examined were divided into two groups in number in accordance with each $F_2$ segregation ratio. Whether or not said two groups are actually in accordance with the $F_2$ segregation ratio, they were examined for the presence of an acid taste.
2) $F_2$ segregation ratio:
Control by one dominant allele = 3:1.
Control by two dominant alleles = 15:1.
Control by three dominant alleles = 63:1.
Control by two dominant alleles plus one recessive allel = 45:19.
Control by one dominant allele plus two recessive alleles = 36:28 = 9:7.
3) $\chi^2{}_{0.05} = 3.84$.
4) A: the number of individuals at each pH value. B: the cumulative total of individuals in the range of pH 4.0–6.5.
5) The number of individuals at each pH value is the total of (No. A x MR1-No. 1)$F_2$(No. B x MR1-NO. 2)$F_2$ in Table 6.

2. Evaluation of a gene governing flesh texture

As shown in Table 8, the flesh of F1 progeny obtained by crossing of the juicy-type cultivated melon (No. A, B, or C) and the mealy-type self-fertilized $S_2$ generation of MR1 was of juicy-type like their parent cultivated melon. This indicates that juicy texture is inherited dominantly as a character over mealy texture. As shown in Table 9, the segregation ratio of juicy to mealy flesh according to the $F_2$ progeny conforms to 3:1 or 45:19, so that the inheritance of the juicy character is assumed to be controlled by one dominant allele or by two dominant alleles plus one recessive allele.

TABLE 8

The number of individuals of $F_1$, $F_2$, and $F_3$ generations classified based on flesh texture

| | No.AxMR1-No.1 | | No.BxMR1-No.2 | | No.CxMR1-No.3 | |
|---|---|---|---|---|---|---|
| | juicy-type | mealy-type | juicy-type | mealy-type | juicy-type | meal-type |
| $F_1$ | 14 | 0 | 8 | 0 | 10 | 0 |
| $F_2$ | 3 | 1 | 18 | 4 | — | — |
| $F_3$ | 7 | 0 | 9 | 0 | — | — |

1) $F_3$ was obtained by self-fertilization of one individual selected from juicy $F_2$ individuals.

TABLE 9

Evaluation of $\chi_2$ based on $F_2$ segregation ratio with respect to flesh texture

| Combination of crossing Flesh texture Number of | No. BxMR1-No. 2 | | No. AxMr1-No. 1 + No. BxMR1-No. 2 | |
|---|---|---|---|---|
| individuals | Juicy | Mealy | Juicy | Mealy |
| Segregation ratio | 18 | 4 | 21 | 5 |
| 3:1 | 0.545 | | 0.4615 | |
| 15:1 | 5.345X | | 7.4769X | |
| 63:1 | 39.506X | | 52.769X | |
| 45:1 | 1.39 | | 1.36 | |
| 9:7 | 5.844X | | 6.352X | |

1) $F_2$ segregation ratio:
Control by one dominant allele = 3:1.
Control by two dominant alleles = 15:1.
Control by three dominant alleles = 63:1.
Control by two dominant alleles plus one recessive allele = 45:19.
Control by one dominant allele plus two recessive alleles 9:7.
2) $\chi^2{}_{0.05} = 3.84$.

Test Example 3

Changes in characteristics of MR1 by selection were examined in the procedure as described below:

Nine individuals from the self-fertilized $S_3$ generation of MR1 (MR1–$S_3$) were cultured in 1991, and 8 individuals of the self-fertilized $S_4$ generation of MR1 (produced from 10 self-fertilized seeds of a selected individual of MR1–$S_3$) were cultured in 1992. The resulting fruits were examined for pH value (Tables 10 and 11). Whatman pH test papers (pH 3.8–5.5, pH 5.2– 6.8, and pH 6.0–8.1) were used for the pH measurement. Test juices were obtained from 3 parts, i.e. a part of seeds and a seeds-surrounding gelatin-like substance, a part of placenta, and a part of flesh. Whether a sour taste was present or not was determined by tasting the juice from each part, and "–" was assigned to juice free of a sour taste and "+" to juice having a sour taste.

Among the respective parts of MR1-$S_3$, the gelatin-like substance around seeds showed the lowest mean pH value as set forth in Table 10, and there were great differences among the $S_3$ generation in the pH values of the gelatin-like substance around seeds and the flesh. From the 9 individuals, there was selected the individual having the flesh and gelatin-like substance with the lowest pH values (Individual No. 6).

In 1992, the self-fertilized seeds ($S_4$ generation) obtained from the selected individual (Individual No. 6) were sown. From 8 individuals of the $S_4$ population, fruits were harvested and examined for their pH values and total soluble solids contents. The pH values of the flesh from said 8 individuals ($S_4$ generation of MR1) were in the range of pH 4.3–4.8 (mean pH: 4.6). Since the flesh of the $S_3$ generation harvested in the previous year (1991) had a pH value in the range of pH 4.5–5.4 (mean pH: 4.9) as set out in Table 10, Individual No. 6 most remarkably indicated weak acidity as character in flesh.

TABLE 10 pH in the 3 parts of MR1-$S_3$ individuals

| Individual No. | Seeds+gelatin-like substance pH | sour taste | Placenta pH | sour taste | Flesh pH | sour taste | Mean pH |
|---|---|---|---|---|---|---|---|
| 1 | 4.6 | + | 4.9 | + | 4.7 | − | 4.7 |
| 2 | 4.7 | + | 4.9 | + | 4.9 | − | 4.8 |
| 3 | 4.7 | + | 4.8 | + | 4.9 | − | 4.8 |
| 4 | 4.7 | + | 4.8 | + | 5.2 | − | 4.9 |
| 5 | 4.7 | + | 4.8 | + | 5.4 | − | 5.0 |
| 6 | 4.4 | + | 4.8 | + | 4.5 | − | 4.6 |
| 7 | 4.8 | + | 4.7 | + | 4.9 | − | 4.8 |
| 8 | 4.5 | + | 4.8 | + | 4.8 | − | 4.7 |
| 9 | 4.6 | + | 4.8 | + | 5.1 | − | 4.8 |
| Mean | 4.6 | + | 4.8 | + | 4.9 | − | 4.8 |

TABLE 11 pH values of sarcocarp in MR1-$S_4$ individuals

| Individual No. | Flesh pH | total soluble slids content |
|---|---|---|
| 1 | 4.7 | — |
| 2 | 4.8 | 5.0 |
| 3 | 4.6 | — |
| 4 | 4.5 | 7.2 |
| 5 | 4.5 | 7.8 |
| 6 | 4.7 | 7.4 |
| 8 | 4.6 | 7.0 |
| Mean | 4.6 | 6.4 |

EXAMPLES

1. Selection of MR1

Individuals with a sour taste in the gelatin-like substance and placenta were selected from the self-fertilized progeny of MR1 as follows. Five seeds of MR1 were sown in the spring of 1987. Most of the resulting fruits were cracking, so that no fruits could be obtained from some of the individuals. After all, self-fertilized seeds could be obtained from 2 individuals out of the 5 individuals. In 1988, 10 seeds from each of 2 self-fertilized lines (the self-fertilized $S_1$ generation) were sown and cultured. From each of the two lines, one individual with a sour taste in the gelatin-like substance and placenta was selected in 1988. Seeds from this individuals were sown and cultured in 1990, whereby 20 individuals (the self-fertilized $S_2$ generation) were obtained, and one individual with a sour taste in the gelatin-like substance and placenta was selected. Fifteen seeds from this individual were sown and cultured in 1991 (the self-fertilized $S_3$ generation), whereby fruits were obtained from 9 individuals.

2. Crossing of MR1 and cultivated melon

In 1991, the individual of MR1 selected above and a cultivated melon breeding line were hybridized, and $F_1$ seeds were obtained. In the following year, the $F_1$ seeds were sown and cultured. From the $F_1$ individuals thus cultured, fruits were obtained.

Cultivated melons commercially available at present have flesh called "juicy-texture". This juicy-texture can be further divided into 3 types, i.e. "sticky-mealy type," "crisp type," and "melting type." The 3 types of cultivated melon are rich in juicy, and melting type in particular is so rich that juice drips from a cut face of the fruit. The characteristics of the cultivated melon used in the crossing are set forth in Table 12.

TABLE 12

Characteristics of fruit in cultivated melon breeding lines

| No. of cultivated melon breeding lines | No. 1 No. 2 No. 3 No. 4 | No. 5 No. 6 | No. 7 No. 8 |
|---|---|---|---|
| Period of ripening | early-ripening | late-ripening | late-ripening |
| Fruit weight | light | light | light |
| Net | sparse | medium | medium |
| Color of flesh | green | green | green |
| Flesh texture (type) | juicy (sticky-mealy) | juicy (crisp) | juicy (melting) |
| Thickness of flesh | medium | medium | thick |
| Mean soluble solids content | 9.4 | 11.2 | 13.5 |
| Taste of flesh | sweet | sweet | sweet |
| Degree of sour taste | 0 | 0 | 0 |
| pH value | 6.6 | 6.2 | 6.4 |

TABLE 13

Degree of sour taste and pH value of flesh and flesh texture in the $F_1$ generation

| | Number of individual examined | Flesh texture | Degree of sour taste | pH |
|---|---|---|---|---|
| selected individual of MR1 (MR1-$S_3$) | 1 | mealy | 0 | 4.5 |
| Self-fertilized progeny (MR1-$S_4$) | 5 | mealy | 0 | 4.6 |
| Selected individual of No. 1×MR1 | 5 | sticky-mealy | 1 | 4.8 |
| Selected individual of No. 2×MR1 | 10 | sticky-mealy | 1.8 | 4.9 |
| Selected individual of No. 3×MR1 | 7 | sticky-mealy | 0.5 | 5.1 |
| Selected individual of No. 4×MR1 | 10 | sticky-mealy | 1.8 | 4.9 |
| selected individual of No. 5×MR1 | 12 | crisp | 2.9 | 4.7 |
| Selected individual of No. 6×MR1 | 14 | crisp | 2.6 | 4.8 |
| Selected individual of No. 7×MR1 | 10 | melting | 3 | 4.5 |
| Selected individual of No. 8×MR1 | 13 | melting | 3 | 4.6 |

1) The strength of sour taste is indicated as the degree of sour taste which is assigned "0" where no taste is present and "3" where a strong taste is present.

As shown in Table 13, every line in the $F_1$ generation has a sour taste and exhibit the same level of acidity as in the selected individuals of MR1. Hence, it was found that a melon with a sour taste in the flesh can be obtained by crossing of the juicy-type cultivated melon with flesh of neutral pH and mealy-type MR1 of weak acidity.

Effect of the Invention

The present invention provides a novel melon of high value as a commercial product with both sour and sweet tastes, thus bringing a great advantage to the field of agriculture.

What is claimed is:

1. A sour tasting *Cucumis melo* F1 hybrid melon derived from the breeding line MR1 having ATCC Accession No. 97226 produced from a plant wherein said plant is grown from a seed and said plant has at least one dominant allele that produces flesh with a mean pH value below 5.4 and at least one dominant allele for expression of juicy character in flesh, and said plant produces melons of an average weight of less than 1.7 kg.

2. A process for producing a sour tasting melon with at least one dominant allele that produces flesh with a mean pH value below 5.4 and at least one dominant allele for expression of juicy character in flesh comprising: crossing a MR1 having ATCC Accession No. 97226 breeding line *Cucumis melo* plant having at least one dominant allele for expression of a weakly acidic pH value in flesh and at least one recessive allele for expression of mealy character in flesh with a cultivated melon producing plant having at least one recessive allele for expression of a neutral pH value in flesh and at least one dominant allele for expression of juicy character in flesh.

3. A process according to claim 2 wherein the cultivated melon producing plant is selected from the group consisting of Earl's Seine, Andes, Loran, Aurora, Sherry and Homerun.

4. The melon as described in claim 1 wherein said MR1 breeding line has at least one dominant allele for expression of a weakly acidic flesh pH value and at least one recessive allele for expression of mealy flesh character.

5. The melon as described in claim 4 further derived from a cultivated melon plant having at least one recessive allele for expression of a neutral flesh pH value and at least one dominant allele for expression of juicy flesh character.

6. The melon according to claim 5 wherein said cultivated melon plant is selected from the group consisting of Earl's Seine, Andes, Loran, Aurora, Sherry and Homerun.

7. The seed as described in claim 1 wherein said seed produces a plant wherein said plant has at least one dominant allele for the expression of juicy flesh character, at least one dominant allele that produces flesh with a mean pH value below 5.4 and wherein said plant produces melons of an average weight of less than 1.7 kg.

\* \* \* \* \*